United States Patent
Reybuck et al.

(10) Patent No.: US 7,377,968 B2
(45) Date of Patent: May 27, 2008

(54) BLENDS OF ENCAPSULATED BIOCIDES

(75) Inventors: Sarah E. Reybuck, Bryn Mawr, PA (US); Curtis Schwartz, Ambler, PA (US)

(73) Assignee: Rohm and Haas Company, Philadephia, PA (US)

( * ) Notice: Subject to any disclaimer, the term of this patent is extended or adjusted under 35 U.S.C. 154(b) by 0 days.

(21) Appl. No.: 11/715,858

(22) Filed: Mar. 8, 2007

(65) Prior Publication Data

US 2007/0215000 A1    Sep. 20, 2007

Related U.S. Application Data

(60) Provisional application No. 60/782,990, filed on Mar. 16, 2006.

(51) Int. Cl.
    C09D 5/14      (2006.01)
    C09D 5/16      (2006.01)
    A01N 25/26     (2006.01)
    A01N 25/28     (2006.01)
    A01N 43/72     (2006.01)
    A01N 43/80     (2006.01)

(52) U.S. Cl. .............................. 106/18.33; 106/15.05; 106/16; 424/78.09; 424/408; 424/489; 424/490; 428/402.2; 428/402.24; 514/373; 523/122; 523/177

(58) Field of Classification Search ............. 106/15.05, 106/16, 18.33; 424/78.09, 408, 489, 490; 428/402.2, 402.24; 514/372, 373; 523/122, 523/177; 548/213
See application file for complete search history.

(56) References Cited

U.S. PATENT DOCUMENTS

| | | | |
|---|---|---|---|
| 4,253,877 A | 3/1981 | Miale et al. | |
| 5,127,934 A * | 7/1992 | Mattox | 504/156 |
| 5,378,413 A | 1/1995 | Mihm et al. | |
| 6,090,399 A * | 7/2000 | Ghosh et al. | 424/409 |
| 6,096,225 A * | 8/2000 | Yang et al. | 210/755 |
| 6,149,927 A * | 11/2000 | Ghosh | 424/405 |
| 6,221,374 B1 * | 4/2001 | Ghosh et al. | 424/405 |
| 6,291,549 B1 * | 9/2001 | Mechtel et al. | 523/122 |
| 6,365,066 B1 | 4/2002 | Podszun et al. | |
| 6,610,282 B1 * | 8/2003 | Ghosh | 424/78.09 |
| 6,676,954 B2 * | 1/2004 | Dai et al. | 424/405 |
| 6,905,698 B1 * | 6/2005 | Aldcroft et al. | 424/405 |
| 2002/0001618 A1 * | 1/2002 | Dai et al. | 424/468 |
| 2003/0194491 A1 | 10/2003 | Gold et al. | |
| 2004/0234603 A1 | 11/2004 | Baum et al. | |
| 2006/0063001 A1 | 3/2006 | Hart et al. | |

FOREIGN PATENT DOCUMENTS

| | | | |
|---|---|---|---|
| EP | 679333 A2 * | 11/1995 | |
| JP | 5-320002 A * | 12/1993 | |
| JP | 200253412 A * | 2/2002 | |

* cited by examiner

Primary Examiner—Anthony J. Green
(74) Attorney, Agent, or Firm—Thomas D. Rogerson

(57) ABSTRACT

The present invention relates to blends of encapsulated biocides with free biocides. In particular, the present invention relates to blends of encapsulated 4,5-dichloro-2-n-octyl-3(2H)-isothiazolone ("DCOIT") with free biocides. The invention also relates to marine antifouling coatings and paints incorporating free biocides and encapsulated DCOIT, and using the free biocides and encapsulated DCOIT in marine antifouling coatings and paints.

10 Claims, No Drawings

BLENDS OF ENCAPSULATED BIOCIDES

This application claims the benefit of priority under 35 U.S.C. §119(e) of U.S. Provisional Patent Application No. 60/782,990 filed on Mar. 16, 2006.

The present invention relates to blends of encapsulated biocides with free biocides. In particular, the present invention relates to blends of encapsulated 4,5-dichloro-2-n-octyl-3(2H)-isothiazolone ("DCOIT") with free biocides. The invention also relates to marine antifouling coatings and paints incorporating free biocides and encapsulated DCOIT, and using the free biocides and encapsulated DCOIT in marine antifouling coatings and paints.

Marine coating and paint manufacturers customarily add biocides to the paint to prevent or inhibit unwanted infestation of the paint films by microorganisms such as, for example, a) soft fouling organisms such as, for example, fungi, such as molds and yeasts, and also by bacteria, algae, and cyanobacteria and b) hard fouling organisms such as, for example, barnacles, shrimp, and tube worms, when these paints are applied on a vessel or underwater structure such as a pier.

The efficacy of biocides in marine antifoulant coatings depends on concentration and flux of biocide from the coatings' surface. Ideally, biocides are released at rates that are above their minimum effective level but not so high that biocide is released wastefully. In reality, biocides formulated into marine antifoulant paints are often released from the films at high initial rates which gradually decrease to uneffective levels over time. The high initial release rate and change in rate over time can be due to changes in concentration gradient or the plasticizing effect of some organic biocides on paint films. A method to control release rates over time is desirable to maximize the dosage and effective lifetime of the biocide in the paint film.

There are many examples of microencapsulated biocides used in paint compositions. See, for example, U.S. Pat. No. 6,365,066 which describes the use of a variety of microencapsulated biocides in combination with film forming polymers. However, these compositions do not address the problem of ensuring that there is sufficient biocide available to provide initial control of microorganisms.

One biocide that has been investigated for use in marine antifoulant paints and coatings is DCOIT. DCOIT has the advantage of low solubility in water and high solubility in xylene, a solvent often used in such paints. Unfortunately, the low water solubility still does not prevent DCOIT from leaching out of the paint film when the film is immersed in water. In addition, DCOIT is known to plasticize paint films, that is, lower the glass transition temperature ("Tg") of many of the polymeric binders used in the paint. Such plasticization often results in an increase in the drying time of the antifoulant paint. These properties have led paint manufacturers desiring to add DCOIT to marine paints to consider encapsulating the DCOIT to reduce leaching and the effect on Tg and/or drying time. Because xylene is a common solvent or base for marine paints, unless the DCOIT capsules are essentially impermeable to xylene, the DCOIT may leak out of the capsules and react with the paint binders. This results in viscosity increases in certain paint formulations or undesirable plasticizing of the paint film. If the microcapsule is too permeable to water, the DCOIT may be leached away from the paint binder shortly after the paint film is applied rendering the paint vulnerable to attack by microorganisms at too early a stage in its service life. Accordingly, there is a need for improved marine antifoulant paint compositions in which the balance between free DCOIT and encapsulated DCOIT is such that the amount of free DCOIT available is high enough to control fouling organisms but low enough to ensure that the Tg of the paint film is not reduced to a level wherein the integrity of the paint film is compromised.

Encapsulation within a crosslinked polymer shell can be used to control the release rate of biocides such as DCOIT into a paint film. Since the biocide is no longer free, its concentration within the paint film is low, so problems with high initial concentration gradients and plasticization are alleviated. The release rate will be steadier over time. The release rate of biocide out of the microcapsules can be controlled by varying microcapsule shell wall chemistry, particle size, shell wall thickness, degree of shell wall crosslinking, presence of solvent in the core, and others. One difficulty with utilizing encapsulation is that in order to provide a paint film with long-term resistance to fouling organisms the release rate of biocide from the microcapsules must be slow. Unfortunately, this results in very low initial concentrations of free biocide. As a result, initial control of fouling organisms is limited.

We have discovered that blending of microcapsules with free biocide can be used to fine tune the overall flux of free biocide in the paint film. One embodiment of the invention is a coating composition comprising:
  a. a microencapsulated biocide comprising an isothiazolone biocide or antifouling agent as a core material encapsulated in a wall material that is essentially impermeable to xylene and from which water can leach the biocide from the wall material;
  b. free isothiazolone biocide or antifouling agent;
  c. a film forming polymer; and
  d. one or more solvents;
  wherein the concentration of free isothiazolone biocide or antifouling agent is from 0.25 percent, by weight of the composition, up to a concentration that does not reduce the glass transition temperature of the film forming polymer by more than 20° C. as determined by differential scanning calorimetry.

Another embodiment of the invention is a coating composition comprising:
  a. a microencapsulated biocide comprising an isothiazolone biocide or antifouling agent as a core material encapsulated in a wall material that is essentially impermeable to xylene and from which water can leach the biocide from the wall material;
  b. free isothiazolone biocide or antifouling agent;
  c. a film forming polymer; and
  d one or more solvents;
  wherein the concentration of free isothiazolone biocide or antifouling agent is from 0.25 percent, by weight of the composition, up to a concentration that does not result in an increase in drying time of the composition.

Unless otherwise specified, all percentages are percent by weight and all ranges are continuous and combinable.

A specific application of blends of encapsulated biocides with free biocides is for the encapsulation of DCOIT for use in marine antifoulant paints. Other potential applications of the coating compositions are in architectural coatings, plastics, wood preservation, and other areas of materials preservation.

In one embodiment of this invention, the microcapsule shell or wall material is designed to be essentially impermeable to xylene. For purposes of this invention, the term "essentially impermeable" means that when contacted with xylene for a period of 90 days at 45° C. less than 20% of an encapsulated biocide is released. This affords good "in-can" stability, and reduces the tendency for the DCOIT to leach from the capsules and interact with or plasticize the paint binders in the dried marine film. The microcapsule shell should also be permeable to water. To achieve a good release rate of the microencapsulated DCOIT, the shell materials should be inherently hydrophilic such that they gradually release DCOIT to the surface of the marine coating in the presence of water and, more particularly, saltwater. In another embodiment of the invention, to enhance saltwater release, certain miscible organic solvents having partial water solubility, that is, solubility in water of from 0.1% to 5% at 25° C., are encapsulated with the DCOIT, to enhance the rate with which DCOIT is released from the film in water. In some embodiments, solvents such as dibasic esters, polyglycols and glycol ether acetates, and isobutyl isobutyrate can be used to form miscible DCOIT blends for encapsulation.

While the discussion herein addresses the encapsulation of DCOIT, those skilled in the art will recognize that other derivatives and analogues of DCOIT and combinations thereof with other biocides could be processed in a similar manner. In particular, other hydrophobic isothiazolones having low water solubility (e.g., less than 2% and more particularly less than 1% in water at room temperature) such as 2-n-octyl-3(2H)-isothiazolone ("OIT") and benzisothiazolone ("BIT") and their alkyl derivatives can be encapsulated alone or in combination with one another or other biocides using the teachings herein. In addition, other hydrophobic biocides, including antifouling agents, with water solubility of less than 2%, such as, for example, triphenylboronpyridine, Diclofluanide, Chlorothalonil, Irgarol, Folpet, TCMBT, and diuron, are applicable for use in the invention.

DCOIT can be encapsulated in a number of wall materials to provide xylene in-can stability and to provide sustained release of the DCOIT upon exposure to water. In a particular embodiment of the invention, the microcapsules are able to limit the release of the encapsulated DCOIT to less than 10% and preferably less than 5% in xylene at room temperature for 90 days. In other embodiments, the xylene impermeability is such that less than 10% and preferably less than 5% of DCOIT is released at 45° C. over 90 days. In a further embodiment, less than 10% of DCOIT is released at 45° C. over one year.

In accordance with one embodiment of the invention a microcapsule having a wall formed from a hydrolyzed polyvinyl acetate and phenolic resin is used for this purpose. For purposes of this invention, the term "PVA" means partially or fully hydrolyzed polyvinyl acetate. In the case of microcapsules formed using partially hydrolyzed polyvinyl acetate, the hydrophilic character of the capsule shell can be adjusted by varying the amount of partially hydrolyzed PVA that is incorporated in the wall. In one embodiment, the PVA and the phenolic resin components (e.g., urea-rescorcinol-formaldehyde) are incorporated into the capsule shell in the amount of from about 4 to about 8 parts by weight partially hydrolyzed PVA and about 20 to 30 parts phenolic resin. The encapsulation procedure for making these microcapsules is well known in the art and is illustrated in Example 1. As illustrated in this example, to prevent the DCOIT from reacting with the wall materials, the DCOIT is mixed with a solvent diluent such as a substituted aromatic solvent like SAS 310 from Nisseki Chemical.

An amino-formaldehyde microcapsule (e.g. a melamine-formaldehyde ("MF") shell provides very stable microcapsules impermeable to xylene, but tends to be too impermeable in water to provide good bio-efficacy for use in conventional antifouling paints. It has been found that by optimizing the shell thickness, a balance of the desired properties of the microcapsules can be achieved. In one embodiment of the present invention, control of microcapsule shell thickness by particle size distribution and shell-to-core ratios contributes diffusion performance or sustained release characteristics. In one embodiment a microencapsulated DCOIT based on an amino-urea-formaldehyde shell system, the target wall thickness is about 0.1 to about 0.2 micron, or the shell to core ratio is about 0.03/1 to 0.05/1 by weight depending on the mean capsule diameter and overall capsule size distribution profile.

Partially hydrolyzed PVA functions as a dopant in the amino-urea formaldehyde wall. In accordance with one embodiment of the invention an agent referred to herein as a "dopant" is incorporated in the microcapsule wall to enhance the ability of water to leach the DCOIT from the capsule. Representative examples of dopants include partially and fully hydrolyzed PVAs, hydroxylethylcellulose, hydroxypropylcellulose, methylcellulose, hydroxyethylmethylcellulose, hydroxypropylmethylcellulose, hyroxybutylmethylcellulose, ethylhydroxyethylcellulose and polyethylene glycols. While the amount of dopant used will vary with the nature and thickness of the wall, in a particular embodiment the dopants are incorporated into the wall in an amount of about 2 to about 10% by weight based upon the weight of the wall materials. For capsules having thick walls, the amount of required dopant is expected to be more than the effective amount for thinner wall capsules.

In order to enhance water release or extraction of the DCOIT, in one embodiment of the invention, the DCOIT is mixed with a partially water miscible solvent. Examples of partial water miscible solvents include, for example, esters and ethers and, more particularly, dibasic esters such as dimethyl adipate, or a blend of diisobutyl adipate, diisobutyl glutarate and diisobutyl succinate, polyglycol P-1200, and glycol ether EB acetate. Miscible organic solvents having partial water solubility in the range of approximately 0.5 to 5% in water are used in one embodiment of the invention. The upper range on the water solubility is not an absolute limit but reflects that if the solvent is more water soluble, it may move into the continuous phase and not remain with the DCOIT to enhance its water leachability. High boiling hydrophilic solvents, for example, having boiling points above 175° C. are desirable to use. If the boiling point of this solvent is too low, the solvent is difficult to retain in the microcapsule during the capsule drying operation. In a particular embodiment the higher boiling partially water miscible solvent is incorporated into the core in an amount of about 5 to about 50% and in other embodiments in an amount of about 10 to 25% by weight based upon the weight of the DCOIT.

In some embodiments of the invention, a dual walled capsule is used. In particular a dual encapsulation process with a first interfacial capsule wall of acrylic polymer and second wall of PVA-urea-resorcinol-gluteraldehyde ("PVA-URG") can be used as illustrated in more detail in Example 3. The dual acrylic-PVA-URG system is advantageous because it provides a formaldehyde free product. Encapsulation based on PVA-URG or acrylic alone typically results in quite leaky capsules that are difficult to recover as a powder. However, combining the two systems to form hybrid capsule shells has resulted in dry free flow capsule powders.

Another embodiment of the present invention, uses a dual encapsulation process with a first interfacial capsule wall of acrylic polymer and PVA-urea-resorcinol-formaldehyde ("PVA-URF") polymer is illustrated in Example 4. In still another embodiment of the present invention, dual wall microcapsules are formed comprising a first wall that is an interfacial reaction product of an aromatic polyisocyanate, a second wall of PVA-URF condensation polymer is illustrated in Example 5. Other microcapsule wall systems that can be used in other embodiments of the present invention, include a melamine-formaldehyde ("MF") shell capsule further re-encapsulated with PVA-URF (Example 6); an MF shell capsules re-encapsulated with PVA-URG polymer (Example 7); a PVA-URF shell capsule re-encapsulated with an MF process; a hydrophilic shell comprising gelatin-gum arabic as a first shell and a second shell of MF or a URF condensation polymer (Examples 8 and 9).

Regarding the dual wall systems, the MF provides significant improvement in xylene stability while the PVA-URF or PVA-URG wall provides additional hydrophilicity in the shell to facilitate diffusion of the DCOIT in an aqueous environment. The dual wall system provides shell strength to minimize capsule damage during paint formulation and spray application of the paint. The ultimate shell characteristics for microencapsulated DCOIT are achieved by adjusting the thickness of the two wall materials to afford a balance of xylene stability and diffusion of DCOIT in seawater.

In another embodiment of the invention, the DCOIT is first encapsulated in a thin (e.g., less than about 0.1 micron) MF wall, and then further encapsulated in a PVA wall as described above. In this case the use of the solvent diluent like the SAS 310 may not be necessary for the encapsulation using the PVA-URF system since the MF wall prevents the DCOIT from reacting with the wall components. Thus, this dual encapsulation process allows the DCOIT to be encapsulated without the diluting effect of solvent and therefore affords a more cost effective product. Of course, the partially water miscible solvent may continue to be used with the DCOIT to enhance water leachability.

In one embodiment of the present invention, multi-shell microcapsules comprising an interfacial first wall with the reaction of an aromatic polyisocyanate, a second shell of gelatin-gum arabic and a third overcoat capsule wall of MF (Example 10). The 3-wall system of isocyanate/gelatin-gum arabic/MF is just another method of controlling capsule-wall permeability in an aqueous environment. The isocyanate-gelatin interface reduces premature diffusion of the DCOIT in the xylene-based paints. The interfacial reaction of polyisocyanate in conjunction with the PVA-URF provides another method of microencapsulating DCOIT. The interfacial skin of polyurethane or polyurea formed by the reaction of the isocyanate with the PVA or a polyamine provides an additional barrier for improving capsule stability in the xylene based MAF paints.

In accordance with one embodiment of the invention, the microcapsules should be small in order to be used in spray applications and to provide better distribution of the active ingredient in the paint film. In one embodiment, the capsule size range is about 5 microns to about 40 microns, and more typically about 5 microns to about 20 microns. Distribution of the biocide improves with smaller capsules such as less than 10 microns.

In one embodiment, the microcapsules are dried before incorporating them into the paint formulation. Any conventional process for drying microcapsules including spray drying can be used for this purpose. However, for some paints it is possible to incorporate the microcapsules into the paint without drying. This is particularly true with water based paints.

In accordance with an embodiment of this invention, the encapsulated biocide is combined with a film forming polymer or binder such as the film forming polymers and binders that have been proposed for use in marine paints, gel coats, and similar paints (e.g., natural or synthetic resin or rosin binders) to provide coating compositions. In one embodiment of the invention, marine antifouling paint compositions can be prepared. Such paints can be prepared by incorporating the free biocide and the microcapsules described herein into the paint in an amount that is sufficient to impart the desired antifouling properties. Such amounts can be readily determined empirically by those skilled in the art. Examples of a marine paints reported in the literature that are useful herein may contain from 5 to 50% by weight, or in other cases from 10 to 25% by weight, xylene or another solvent base, from 20 to 30% by weight zinc resinate to plasticize the resin binder, from 10 to 20% by weight resin binder, optionally from 0 to 50% , or in other cases about 30 to 40% by weight, cuprous oxide pigment, and 4 to 6% by weight thixotropic viscosity modifier. Another type of marine paint may contain from 15% to 20% of polymer solids (binder), optionally up to 5% rosin, a total of from 10% to 15% biocide, from 30% to 40% pigment, from 1% to 3% additives, and from 30% to 40% solvents, typically xylene. Still another type of marine paint may contain from 15% to 20% polymer solids, optionally up to 5% rosin, from 35% to 50% copper(II) oxide, up to 5% total biocide, from 10% to 15% pigment, from 1% to 3% additives, and from 20% to 30% solvent. Generally, the ingredients are thoroughly mixed as follows: 200 ml of the paint composition is introduced into a tight metallic container of 0.5 L capacity together with 100 ml (bulk volume) of glass beads with a diameter of 2-3 mm. The container is then shaken for 45 minutes on a mechanical shaker. The final paint composition is separated from the glass beads by filtration. The free and the microencapsulated DCOIT biocides are incorporated in the paint in an amount to provide the marine antifouling properties that are desired (e.g., a total of about 1.5% to 30% by weight. The amount required will be a function of the rate at which the free DCOIT is leached from the dried coating film and the rate at which the encapsulated DCOIT is leached from the microcapsules. In one embodiment, the capsules are added in an amount to provide about 2% DCOIT in the dry film. In one embodiment, the free DCOIT is added in an amount of from 0.25% to 15% of the weight of the film forming polymer or binder solids. In another embodiment, the free DCOIT is added in an amount of from 5% to 15%. In still another embodiment, the free DCOIT is added in an amount of from 8% to 12%, preferably about 10%.

The free DCOIT may be added to the compositions of the invention in any convenient form. This includes adding it as a solution wherein the DCOIT is dissolved in a solvent compatible with the compositions. In one embodiment, the DCOIT is added as a solid material. Such a solid material may be, for example, in the form of a powder, flakes, or a melt. One convenient form is to add the material as a technical grade active ingredient such as, for example, Kathon™ 287T microbicide from Rohm and Haas Company.

Other applications for the combination of free and microencapsulated DCOIT may include use as a biocide in latex or oil-based paints and coatings, adhesives, sealants, caulks, mastic and patching materials, building materials, roofing materials such as shingles, plastics, polymer composites, paper processing, paper coatings, wood preservation, cooling water towers, metal working fluids, and as a general preservative. One skilled in the art will modify the compositions for the particular application.

In accordance with another embodiment of the invention, a combination of free DCOIT is combined with two or more microcapsules can be used to provide a composition in which release the biocide occurs at different rates, for example, one microcapsule may be used that releases the biocide after or over a short time period and another microcapsule(s) might be used that releases the biocide after or over a somewhat longer time. These microcapsules may be made of different wall materials or different wall thicknesses in accordance with other embodiments of the invention.

The present invention is further illustrated by the following non-limiting examples. Unless otherwise specified, the source of the DCOIT was Kathon™ 287T biocide. Examples 1-10 describe a number of techniques to encapsulate DCOIT.

EXAMPLE 1

Microencapsulation of DCOIT Containing Solvent Diluent

An aqueous phase is prepared consisting of 160 grams each of a 5% strength aqueous solutions of PVA, (Vinol™ 540 and Vinol™ 125 both manufactured by Air Products) and 300 grams of water. The aqueous phase is heated to 40° C.

The core material is prepared as a mixture of 100 grams of DCOIT (97%) and 100 grams of a substituted aromatic solvent, SAS 310 manufactured by Nisseki Chemical and heated to 40° C. The aqueous phase and the core material are added to a 1-quart Waring Blender jar and the slurry is emulsified at moderate speed for about 15 minutes to produce an oil-in-water emulsion of droplets in the size range of about 10 to 40 microns. The emulsion is transferred to a 1-liter beaker. The slurry is slowly agitated using a turbine impellor while maintaining the temperature at about 40° C. A solution of 4 grams of urea and 10 grams of resorcinol in 60 grams of water is slowly added to the emulsion. A solution of 2 grams sodium sulfate in 30 grams of water is subsequently added to the slurry in drop-wise fashion. A 30 ml 37% formaldehyde solution is added drop-wise followed 10 minutes later by the addition of 20 ml of a 10% sulfuric acid solution over a 5-minute period. The slurry is warmed to 45° C. and after about one hour a solution of 4 g of urea, 6 g of resorcinol, 50 g of water and 20 ml of 37% formaldehyde second addition is added drop-wise. This solution may be divided, with half added in 15 minutes followed by a 15-minute hold period prior to adding the second half. One hour later another solution like the proceeding is added to the slurry in the same fashion. The slurry is heated to 55° C. and allowed to stir for 16 hours. The microcapsule slurry is cooled to ambient temperature and pH adjusted to 7.0 using 10% sodium hydroxide solution. The slurry is then diluted with water and strained using a 125 -150 um sieve to remove encapsulated air and any debris. The slurry is set aside to allow the microcapsules to settle. The supernatant liquid is decanted and microcapsule concentrate is re-slurried with water. A small amount of Syloid 244 silica from W. R. Grace Company is stirred into the slurry; and the microcapsules are vacuum-filtered using Whatman 4.0 paper and tray dried to produce 230 grams of dry free-flowing powder.

EXAMPLE 2

Microencapsulation of Neat DCOIT Biocide

The microencapsulation of neat DCOIT is carried out in an aqueous continuous phase to produce microcapules comprising an amino-formaldehyde shell. An aqueous phase is prepared consisting of 27.5 g of a 3.75% ethylene maleic anhyride co-polymer (manufactured by Zeeland Chemical Company) solution and 30.37 g of water and heated to 45° C. In a separate vessel, 32.5 g of DCOIT 97.5% and is heated to 45° to form a liquid melt. An emulsion is prepared by dispersing the melted DCOIT core material in the aqueous phase using an Ika-Works mixer and high speed turbine with the speed controlled to produce DCOIT droplets mostly in the range of 10-50 um. While maintaining the temperature at 45° C. during the emulsification process, 5.58 grams of Cymel 385 manufactured by Cytec is added to stabilize the emulsion. After about 15 minutes, the agitation speed is reduced and additional 1.79 grams of the Cymel 385 resin is added while maintaining the temperature at around 50° C. After a few minutes, a 5-gram solution of a 5% PVA (Vinyl™ 540 manufactured by Air Products) is added followed a drop-wise addition of 11 grams of a 15% salt solution of potassium dihydrogen phosphate over a 10 minute period. The temperature of the microcapsule slurry is slowly increased to 65° C. and 2.06 grams of urea is added about 1.5 hours after the salt addition. After an additional 4 hours of stirring at 65° C., the slurry is cooled to ambient and the ph adjusted to 7.0 using 45% potassium hydroxide solution. The slurry is diluted 1:1 with water and sieved using a 125 um sieve to remove encapsulated air and any debris. The microcapsules are allowed settle and the supernatant liquid decanted. The microcapsule concentrate is re-slurried in water and the decantation process repeated. The microcapsules are re-slurried with water; vacuum filtered using Whatman 4.0 paper; and tray dried either on the lab bench at ambient conditions or in a warm oven. The resultant microcapsules are a dry-free flowing powder that can be readily incorporated into a marine paint formulation to provide a marine coating in accordance with one embodiment of the invention.

EXAMPLE 3A

Microencapsulation of DCOIT Biocide with a Dual Shell of Acrylic and PVA-urea-resorcinol-gluteraldehyde An internal phase is prepared by mixing together molten DCOIT (150 g) at a temperature of around 50° C., with methyl methacrylate (10 g) 1, 4, butanediol diacrylate (10 g) and trimethylolpropane trimethacrylate (10 g). Just prior to emulsification, tertbutyl perpivalate (1 g) is mixed in to the internal phase. The internal phase is homogenized into water (254 g) containing PVA (Elvanol™ 50-42 manufactured by DuPont) (6 g) using a Waring 1 liter blender for 10 minutes until a stable emulsion is formed. The emulsion is then transferred into a 1-liter beaker with overhead stirring, thermometer and nitrogen supply and deoxygenated with nitrogen for 1 hour while heating to 90° C. The batch is then held at 90° C. for 1.5 hours after nitrogen removal before being cooled down to 45° C. The resulting emulsion contains polymeric particles each comprising a polymeric shell encapsulating the DCOIT having a mean particle size of 19 microns.

The particles of encapsulated DCOIT are then subjected to a secondary treatment at 45° C. involving drop wise additions of aluminum sulfate TG 8.3% (60 g) over 12 minutes, 10 v/v % sulfuric acid (34 g) over 12 minutes, and a mixture of urea (2 g), resorcinol (1.5 g), and water (20 g) over 12 minutes. Then a mixture of 25% gluteraldehyde (5 g) and water (5 g) are added drop wise very slowly over 20 minutes to prevent aggregation. Then a second addition of urea (2 g), resorcinol (1.5 g), and water (20 g) is added over 12 minutes followed by a mixture of 25% gluteraldehyde (5 g) and water (5 g) added drop wise over 12 minutes. Followed by a third addition of urea (2 g), resorcinol (1.5 g), and water (20 g) is added over 12 minutes followed by a mixture of 25% gluteraldehyde (5 g) and water (5 g) added drop wise over 12 minutes. After all additions are made the temperature is increased from 45° C. to 50° C. and held overnight to cure for approximately 16 hours. After cooling and pH neutralization the microcapsules are filtered and dried to produce a fine free flowing powder that can be readily incorporated into a marine paint formulation to provide a marine coating in accordance with one embodiment of the invention.

EXAMPLE 3B

Example 3A is repeated using a solution of sodium sulfate powder (2 g) dissolved in water (30 g) instead of aluminum sulfate. The sodium sulfate solution is added drop wise over 12 minutes. Again, a dry free flowing powder is achieved that can be readily incorporated into a marine paint formulation to provide a marine coating in accordance with one embodiment of the invention.

EXAMPLE 4

Dual Encapsulation Process with a First Interfacial Capsule Wall of Acrylic Polymer and PVA-urea-resorcinol-formaldehyde Polymer An internal phase is prepared by mixing together molten DCOIT (150 g) at a temperature of around 50° C., with methyl methacrylate (10 g) 1, 4, butanediol diacrylate (10 g) and trimethylolpropane trimethacrylate (10 g). Just prior to emulsification, tertbutyl perpivalate (1 g) is mixed in to the internal phase. The internal phase is homogenized into water (453 g) containing PVA (Elvanol™ 50-42) (6 g) and (Elvanol™ 71-30) (6 g) using a Waring 1 liter blender for 8 minutes until a stable emulsion is formed. The emulsion is then transferred into a 1.5-liter beaker with overhead stirring, thermometer and nitrogen supply and deoxygenated with nitrogen for 1 hour while heating to 90° C. The batch is then held at 90° C. for 1.5 hours after nitrogen removal before being cooled down to 40° C. The resulting emulsion contains polymeric particles each comprising a polymeric shell encapsulating the DCOIT having a mean particle size of 19 microns. The particles of encapsulated DCOIT are then subjected to a secondary treatment at 40° C. involving drop wise addition of a mixture of urea (3 g), resorcinol (7.5 g), and water (45 g) over 12 minutes. Then a solution of sodium sulfate powder (1.5 g) and water (22.5 g) is added drop wise over 10 minutes. Then a 37% solution of formaldehyde (22.5 ml) is added drop wise over 10 minutes. After a 10-minute hold at 40° C., 10 v/v % sulfuric acid is added drop wise over 6 minutes. The batch is then stirred and slowly heated to 45° C. over 1 hour. Then a second addition of a solution of urea (3 g), resorcinol (4.5 g), water (37.5 g) and 37% formaldehyde (15 ml) is divided in half and added over 12 minutes followed by the second half after a 15 minute hold at 45° C. The batch is then stirred and slowly heated to 48° C. over 1 hour. A third addition of urea (3 g), resorcinol (4.5 g), water (37.5 g) and 37% formaldehyde (15 ml) is added over 12 minutes. After all additions are made the temperature is increased from 48° C. to 50° C. and held overnight to cure for approximately 16 hours. After cooling and pH neutralization the microcapsules are filtered and dried to produce a dry product that can be readily incorporated into a marine paint formulation to provide a marine coating in accordance with one embodiment of the invention.

EXAMPLE 5

Dual Wall Microcapsules Comprising an Interfacial First Wall with the Reaction of an Aromatic Polyisocyanate, a Second Shell of PVA-urea-resorcinol-formaldehyde Condensation Polymer An internal phase is prepared by mixing together molten DCOIT (90 g) at a temperature of around 50° C., with Desmodur™ L 75 (Bayer) (10 g). The internal phase is homogenized into water (302 g) containing PVA (Elvanol™ 50-42) (4 g) and (Elvanol™ 71-30) (4 g) using a Waring 1 liter blender for 13 minutes until a stable emulsion is formed. The emulsion is then transferred into a 1-liter beaker with overhead stirring and thermometer. The batch is then heated to 50° C. and a solution of triethylene diamine (0.5 g) and water (10 g) is added drop wise. The batch is then held at 50° C. overnight. The resulting emulsion contains polymeric particles each comprising a polymeric poly urea shell encapsulating the DCOIT having a mean particle size of 16 microns. The particles of encapsulated DCOIT are then subjected to a secondary treatment at 40° C. involving drop wise addition of a mixture of urea (2 g), resorcinol (5 g), and water (30 g) over 12 minutes. Then a solution of sodium sulfate powder (1 g) and water (15 g) is added drop wise over 6 minutes. Then a 37% solution of formaldehyde (15 ml) is added drop wise over 7 minutes. After a 10-minute hold at 40° C., 10 v/v % sulfuric acid is added drop wise over 5 minutes. The batch is then stirred and slowly heated to 45° C. over 1 hour. Then a second addition of a solution of urea (2 g), resorcinol (3 g), water (25 g) and 37% formaldehyde (10 ml) is divided in half and added over 12 minutes followed by the second half after a 15 minute hold at 45° C. The batch is then stirred and slowly heated to 48° C. over 1 hour. A third addition of urea (2 g), resorcinol (3 g), water (25 g) and 37% formaldehyde (10 ml) is added over 12 minutes. After all additions are made the temperature is increased from 48° C. to 50° C. and held overnight to cure for approximately 16 hours. After cooling and pH neutralization the microcapsules are filtered and dried to produce a lumpy isolation.

EXAMPLE 6

MF Shell Capsules Re-encapsulated with PVA-URF Polymer

An internal phase is prepared by melting DCOIT (260 g) at a temperature of around 50° C. The internal phase is homogenized into an aqueous A Solution consisting of 110.0 g of a 3.75% ethylene maleic anhydride copolymer solution and 121.48 g of water using a Waring 1 liter blender. While maintaining the temperature of around 50° C. during the emulsification process, Cymel™ 385 (22.33 g) manufactured by Cytec is added to stabilize the emulsion. After about 15 minutes, the agitation is reduced and 10-50 um droplets are formed. The emulsion is then transferred into a 1-liter beaker with overhead stirring and thermometer. Then a 15% salt solution (44 g) of potassium dihydrogen phosphate is added drop wise. The batch is then heated to 65° C. over 1.5 hours and held for 4 hour then cooled. The resulting emulsion contains polymeric particles each comprising a polymeric amino-formaldehyde shell encapsulating the DCOIT having a mean particle size of 16 microns.

The particles of encapsulated DCOIT slurry are then divided in half. This (272 g) fraction is subjected to a secondary treatment at 45° C. involving drop wise addition of a mixture of urea (3 g), resorcinol (3 g), and water (30 g) over 10 minutes. Then a 37% solution of formaldehyde (18 ml) is added drop wise over 7 minutes. After a 10-minute hold at 45° C., 10 v/v % sulfuric acid (10 ml) is added drop wise over 5 minutes. The batch is then stirred at 45° C. over 1 hour. Then a second addition of a solution of urea (3 g), resorcinol (7 g), water (30 g) and 37% formaldehyde (25 ml) is divided in half and added over 12 minutes followed by the second half after a 15 minute hold at 45° C. The batch is then stirred and slowly heated to 55° C. over 1 hour. Then heated to 60° C. for 3 hours and cooled. After cooling and pH neutralization the microcapsules are filtered and dried to produce a fine free flowing powder that can be readily incorporated into a marine paint formulation to provide a marine coating in accordance with one embodiment of the invention.

EXAMPLE 7A

MF Shell Capsules Re-encapsulated with PVA-urea-resorcinol-gluteraldehyde Polymer An internal phase is prepared by melting DCOIT (260 g) at a temperature of around 50° C. The internal phase is homogenized into an aqueous solution consisting of 110.0 g of a 3.75% ethylene maleic anhydride copolymer solution and 121.48 g of water using a Waring 1 liter blender. While maintaining the temperature of around 50° C. during the emulsification process, Cymel 385 (22.33 g) manufactured by Cytec is added to stabilize the emulsion. After about 15 minutes, the agitation is reduced and 10-50 um droplets are formed. The emulsion is then transferred into a 1-liter beaker with overhead stirring and thermometer. Then a 15% salt solution (44 g) of potassium dihydrogen phosphate is added drop wise. The batch is then heated to 65° C. over 1.5 hours and held for 4 hour then cooled. The resulting emulsion contains polymeric particles each comprising a polymeric amino-formaldehyde shell encapsulating the DCOIT having a mean particle size of 16 microns. The particles of encapsulated DCOIT slurry are then divided and half are filtered to a wet cake of 80.51% (127.5 g dry wt.). The wet cake is then re-suspended in a mixture of water (254 g ) containing PVA (Elvanol™ 50-42) (6 g) and subjected to a secondary treatment at 45° C. involving drop wise additions of aluminum sulfate TG 8.3% (60 g) over 12 minutes, 10 v/v % sulfuric acid (34 g) over 12 minutes, and a mixture of urea (2 g), resorcinol (1.5 g), and water (20 g) over 12 minutes. Then a mixture of 25% gluteraldehyde (5 g) and water (5 g) are added drop wise very slowly over 20 minutes to prevent aggregation. Then a second addition of urea (2 g), resorcinol (1.5 g), and water (20 g) is added over 12 minutes followed by a mixture of 25% gluteraldehyde (5 g) and water (5 g) added drop wise over 12 minutes. Followed by a third addition of urea (2 g), resorcinol (1.5 g), and water (20 g) is added over 12 minutes followed by a mixture of 25% gluteraldehyde (5 g) and water (5 g) added drop wise over 12 minutes. After all additions are made the temperature is increased from 45° C. to 50° C. and held overnight to cure for approximately 16 hours. After cooling and pH neutralization the microcapsules are filtered and dried to produce a fine free flowing powder that can be readily incorporated into a marine paint formulation to provide a marine coating in accordance with one embodiment of the invention.

EXAMPLE 7B

Example 7A is repeated using a solution of sodium sulfate powder (2 g) dissolved in water (30 g) instead of aluminum sulfate. The sodium sulfate solution is added drop wise over 12 minutes. Again, a dry free flowing powder was produced that can be readily incorporated into a marine paint formulation to provide a marine coating in accordance with one embodiment of the invention.

EXAMPLE 8

Dual Encapsulation with Gelatin/Gum Arabic as the First Shell and Melamine Resin as the Second Wall In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring. Adjust the pH to clear the solution with 10% NaOH (~pH 7). Adjust the pH to 4.1 with 10% Acetic Acid. Warm 40 grams DCOIT to 50-60° C. to melt. Transfer the Gelatin/Gum Arabic solution to a warm blender jar and add the DCOIT melt. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25° C. One should observe a substantial wall and no free polymer. Continue cooling to 15° C., at which time 10 grams of 25% gluteraldehyde is added. After adding more ice, stir overnight, allowing the reaction to warm to room temperature. Decant 2 times by letting capsules settle and rinsing with 300 ml deionized water. Capsules can be isolated at this point by filtering and adding 1.5 grams Aerosil 972R to the filter-cake and shaking in a wide-mouth bottle to mix well. The powder is laid out on a paper towel to bench-dry overnight. This resulted in a free flowing powder with single (droplet) capsules as well as some aggregates.

A second wall can be added by filtering the twice-decanted slurry. The wet filter-cake is re-suspended in 25 grams of 3.75% EMA solution and 50 ml deionized water. Begin heating to 50° C. and while dripping in 3 grams Cymel 385 in 12 ml deionized water. At 50° C., drop-wise, add 10 grams 15% dihydrogen phosphate solution. Heat to 65° C. and hold over night. Cool to room temperature and adjust the pH to 7.0 with 45% Potassium Hydroxide solution. Filter, and wash with deionized water. Spread out on a paper towel to dry. This resulted in a free flowing powder with single (droplet) capsules as well as some aggregates.

EXAMPLE 9

Dual Encapsulation with Gelatin/Gum Arabic as the First Shell and Urea-Resorcinol-Formaldehyde Polycondensate as the Second Wall In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring. Adjust the pH to clear the solution with 10% NaOH (~pH 7). Adjust the pH to 4.1 with 10% Acetic Acid. Warm 40 grams DCOIT to 50-60° C. to melt. Transfer the Gelatin/Gum Arabic solution to a warm blender jar and add the DCOIT melt. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25°. One should observe a substantial wall and no free polymer. Continue cooling to 15° C., at which time 10 grams of 25% gluteraldehyde is added. After adding more ice, stir overnight, allowing the reaction to warm to room temperature. Decant 2 times by letting capsules settle and rinsing with 300 ml deionized water. Capsules can be isolated at this point by filtering and adding 1.5 grams Aerosil™ 972R (Degussa) to the filter-cake and shaking in a wide-mouth bottle to mix well. The powder is laid out on a paper towel to bench-dry overnight. This resulted in a free flowing powder with single (droplet) capsules as well as some aggregates. A second wall can be added by filtering the twice-decanted slurry. The wet filter-cake is re-suspended in 25 grams of 3.75% EMA solution and 50 ml deionized water. Begin heating to 50° C. and while dripping in 2 grams Urea and 0.2 grams resorcinol in 10 ml deionized water. At 50° C., drop-wise, add 5 grams 37% Formaldehyde solution then 10 grams 15% dihydrogen phosphate solution. Heat to 55° C. and hold over night. Cool to room temperature and adjust the pH to 7.0 with 45% Potassium Hydroxide solution. Filter, and wash with deionized water. Spread out on a paper towel to dry. This resulted in a free flowing powder with single (droplet) capsules as well as some aggregates.

EXAMPLE 10

Multi-shell Microcapsules Comprising Polyurethane/Polyurea, Gelatin/Gum Arabic and Melamine Resin In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring. Adjust the pH to clear the solution with 10% NaOH (~pH 7). Adjust the pH to 4.1 with 10% Acetic Acid. Warm 40 grams DCOIT to 50-60° C. to melt. Add 4 grams Desmondure™ CB-75 and mix well. Transfer the Gelatin/Gum Arabic solution to a warm blender jar and add the DCOIT solution. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25° C. One should observe a substantial wall and no free polymer. Continue cooling to 15° C., at which time 10 grams of 25% gluteraldehyde is added. After adding more ice, stir overnight, allowing the reaction to warm to room temperature. Decant 2 times by letting capsules settle and rinsing with 300 ml deionized water. Capsules can be isolated at this point by filtering and adding 1.5 grams Aerosil 972R to the filter-cake and shaking in a wide-mouth bottle to mix well. The powder is laid out on a paper towel to bench-dry overnight. This resulted in a free flowing powder with single (droplet) capsules as well as some aggregates. A third wall can be added by filtering the twice-decanted slurry. The wet filter-cake is re-suspended in 25 grams of 3.75% EMA solution and 50 ml deionized water. Begin heating to 50° C. and while dripping in 3 grams Cymel 385 in 12 ml deionized water. At 50° C., drop-wise, add 10 grams 15% dihydrogen phosphate solution. Heat to 65° C. and hold over night. Cool to room temperature and adjust the pH to 7.0 with 45% Potassium Hydroxide solution. Filter, and wash with deionized water. Spread out on a paper towel to dry. This results in a free flowing powder with single (droplet) capsules as well as some aggregates.

EXAMPLE 11

Effect of DCOIT on Polymer Tg

Several films of two test polymers were prepared by solvent casting. The films were dried for various times at ambient temperature and 60° C. The Tg's of the films were measured by DSC, and on the same day the residual solvent was extracted from the films for quantification via GC analysis. The percent solvent remaining and Tg after various drying times and temperatures were determined for the test polymers. Residual solvent was found in all of the films, causing the measured Tg's to be lower than the expected Tg. Results are shown in Table I. Polymer 1 was Acryloid™ B-72 polymer (Rohm and Haas Company) cast from toluene and Polymer 2 was Vinylite™ VYHH polymer cast from methyl isobutyl ketone.

TABLE I

Residual Solvent and Tg* of Polymer Films

| Drying Time/ Temperature | Polymer 1 (Tg = 40° C.) | | Polymer 2 (Tg = 72° C.) | |
| --- | --- | --- | --- | --- |
| | % Toluene | Tg (° C.) | % MIBK | Tg (° C.) |
| 1 day @ ambient | 10.4 | −3.0 | 14.6 | 9.4 |

TABLE I-continued

Residual Solvent and Tg* of Polymer Films

| Drying Time/ Temperature | Polymer 1 (Tg = 40° C.) | | Polymer 2 (Tg = 72° C.) | |
|---|---|---|---|---|
| | % Toluene | Tg (° C.) | % MIBK | Tg (° C.) |
| 1 day @ 60° C. | 6.3 | 9.7 | 9.3 | 29.5 |
| 2 days @ 60° C. | 4.3 | 20.8 | 8.6 | 34.9 |
| 7 days @ 60° C. | 2.9 | 29.5 | 7.0 | 39.9 |
| 14 days @ 60° C. | 1.9 | 33.6 | 6.2 | 42.4 |
| 21 days @ 60° C. | 1.6 | 34.4 | 5.5 | 47.9 |
| 6 wks @ ambient | 6.9 | 11.1 | 9.0 | 31.5 |

*Tg reported is the inflection point of transition range. Heating rate was 20° C. per minute.

A series of films of the two test polymers containing DCOIT at various levels were prepared by solvent casting. After a period of drying at ambient temperature, the Tg, % residual solvent, and % DCOIT were measured in the films. The results are shown in Table II.

TABLE II

Analysis of Films Containing RH-287 and Residual Solvent

| Polymer 1 | | | Polymer 2 | | |
|---|---|---|---|---|---|
| % Toluene | % DCOIT | Tg (° C.) | % MIBK | % DCOIT | Tg (° C.) |
| 8.0 | 1.6 | 5.4 | 9.4 | 1.0 | 34.4 |
| 7.5 | 4.0 | 3.5 | 7.1 | 5.1 | 34.9 |
| 5.9 | 8.3 | 0 | 6.1 | 8.8 | 29.1 |
| 3.5 | 12.7 | 0.4 | 2.9 | 16.7 | 26.3 |
| 0.5 | 21.2 | −0.6 | 0.7 | 23.9 | 21.5 |

The measured Tg values in Table II reflect a decrease in Tg due to DCOIT and to residual solvent. In order to be able to quantitate the effect of DCOIT on a polymer film, the solvent effect was subtracted out. For each film containing DCOIT and residual solvent, the Tg expected if the film only contained solvent was calculated from an equation obtained from the linear regression of solvent vs. Tg curve. The measured Tg was then subtracted from the expected, solvent only, Tg to give degrees of Tg change due to the presence of DCOIT. This difference was then subtracted from the intercept (of Tg vs solvent line) to give a corrected Tg.

EXAMPLE 12

Leaching of DCOIT from Polymer Films

Three marine antifoulant paints (ablative type) were prepared with different weight percents of free and encapsulated DCOIT active based on formulation weight. The paints contained (1) 2.0% free DCOIT, (2) 0.25% free DCOIT blended with 1.75% encapsulated DCOIT made with the process of Example 2 except that no PVA was added as a dopant, a lower cure temperature was used, the microcapsule had a thicker shell wall, and lower salt level (potassium dihydrogen phosphate) was used, and (3) 2.0% encapsulated DCOIT made with similar modifications. The paints were applied to polycarbonate test cylinders (with approximately 6.4 cm outer diameter) to give paint film surface areas of 200 cm$^2$ and minimum dry film thicknesses of 100 μm. After drying, the painted surfaces of the cylinders were submerged into a holding tank of synthetic seawater. After the indicated time period, the painted surfaces of the test cylinders were removed from the holding tank and submerged into individual measuring containers containing 1500 mL of fresh synthetic seawater and rotated at 60 r/min for 60 minutes. After the 60 minutes, the cylinders were returned to the holding tank. HPLC was used to measure the concentration of DCOIT in the seawater in the measuring containers and used to calculate the rate of DCOIT leach (in μg/cm$^2$/day) from the paint film surfaces. The results are in Table III.

TABLE III

| sample | | DCOIT leach rate [μg/ (cm$^2$ × day)] | | | |
|---|---|---|---|---|---|
| | day | 0.97 | 3 | 7 | 14 |
| 2.0% (a.i.) free DCOIT | | 27.54 | 7.2 | 1.8 | 0.252 |
| | | 24.84 | 6.66 | 1.26 | 0.18 |
| | avg. | 26.19 | 6.93 | 1.53 | 0.216 |
| 0.25% free DCOIT + 1.75% encapsulated DCOIT | | 2.34 | 0.342 | 1.188 | 0.054 |
| | | 2.16 | 0.522 | 0.576 | 0.018 |
| | avg. | 2.25 | 0.432 | 0.882 | 0.036 |
| 2.0% encapsulated DCOIT | | 0.486 | 0.396 | 0.072 | 0.018 |
| | | 0.864 | 0.216 | 0.054 | 0.018 |
| | avg. | 0.675 | 0.306 | 0.063 | 0.018 |

These data demonstrate that blending of microencapsulated DCOIT with free DCOIT can be used to fine tune the overall flux of biocide from the paint film.

We claim:

1. A coating composition comprising:
   a. a microencapsulated biocide comprising an isothiazolone biocide or antifouling agent as a core material encapsulated in a wall material that is essentially impermeable to xylene and from which water can leach the biocide from the wall material;
   b. free isothiazolone biocide or antifouling agent;
   c. a film forming polymer or binder; and
   d. one or more solvents;
   wherein the concentration of free isothiazolone biocide or antifouling agent is from 0.25 percent, by weight of the composition, up to a concentration that does not reduce the glass transition temperature of the film forming polymer by more than 20° C.

2. The coating composition of claim 1 wherein the microencapsulated biocide comprises 4,5-dichloro-2-n-octyl-3(2H)-isothiazolone.

3. The coating composition of claim 1 wherein the free isothiazolone biocide comprises 4,5-dichloro-2-n-octyl-3 (2H)-isothiazolone.

4. The coating composition of claim 1 wherein the composition comprises two or more microencapsulated biocides or antifouling agents.

5. The coating composition of claim 1 wherein the composition comprises two or more free isothiazolones biocides or antifouling agents.

6. A coating composition comprising:
   a. a microencapsulated biocide comprising an isothiazolone biocide or antifouling agent as a core material encapsulated in a wall material that is essentially impermeable to xylene and from which water can leach the biocide from the wall material;
   b. free isothiazolone biocide or antifouling agent;
   c. a film forming polymer or binder; and
   d one or more solvents;
   wherein the concentration of free isothiazolone biocide or antifouling agent is from 0.25 percent, by weight of the composition, up to a concentration that does not result in an increase in drying time of the composition.

7. The coating composition of claim 6 wherein the microencapsulated biocide comprises 4,5-dichloro-2-n-octyl-3(2H)-isothiazolone.

8. The coating composition of claim 6 wherein the free isothiazolone biocide comprises 4,5-dichloro-2-n-octyl-3(2H)-isothiazolone.

9. The coating composition of claim 6 wherein the composition comprises two or more microencapsulated biocides or antifouling agents.

10. The coating composition of claim 6 wherein the composition comprises two or more free isothiazolones biocides or antifouling agents.

* * * * *